United States Patent
Jacobi (10) Patent No.: US 7,856,977 B2
(45) Date of Patent: Dec. 28, 2010

(54) PART OF AN ELECTRICAL CONNECTING DEVICE

(75) Inventor: Wolfgang Jacobi, München (DE)

(73) Assignee: ODU Steckverbindungssysteme GmbH & Co. KG, Muhldorf (DE)

( * ) Notice: Subject to any disclaimer, the term of this patent is extended or adjusted under 35 U.S.C. 154(b) by 974 days.

(21) Appl. No.: 11/680,364

(22) Filed: Feb. 28, 2007

(65) Prior Publication Data

US 2007/0208451 A1    Sep. 6, 2007

(30) Foreign Application Priority Data

Mar. 2, 2006    (DE) ............... 10 2006 009 733

(51) Int. Cl.
*A62B 9/04* (2006.01)

(52) U.S. Cl. ............ 128/202.27; 439/488; 439/491; 606/1

(58) Field of Classification Search ............ None
See application file for complete search history.

(56) References Cited

U.S. PATENT DOCUMENTS

| 4,155,895 A | 5/1979 | Rohowetz et al. |
| 5,225,816 A * | 7/1993 | Lebby et al. ............... 340/653 |
| 6,259,170 B1 * | 7/2001 | Limoge et al. ............ 307/10.8 |

FOREIGN PATENT DOCUMENTS

| DE | 29 18 806 | 5/1979 |
| DE | 694 14 722 T2 | 10/1993 |

* cited by examiner

*Primary Examiner*—Antonio A Caschera
(74) *Attorney, Agent, or Firm*—Schwabe Williamson & Wyatt, P.C.

(57) ABSTRACT

Part of an electrical connecting device, especially for use in medical technology, with a display device to display an effect on the part resulting from a preparatory step for the use of the part, whereby the display device has a visible field whose colored appearance changes at least in sections as a reaction to the effect resulting from the preparatory measure.

14 Claims, 5 Drawing Sheets

PART OF AN ELECTRICAL CONNECTING DEVICE

CROSS-REFERENCE TO RELATED APPLICATION

The present application claims International Priority under 35 U.S.C. §119 to co-pending German Patent Application No. 102006 009 733.5, filed Mar. 2, 2006, entitled "Teil einer elektrischen Kuppelvorrichtung"; the entire content and disclosure of which are hereby incorporated by reference in its entirety.

TECHNICAL FIELD

Embodiments of the invention relate to apparatus and methods for sorting products. More particularly, various embodiments relate to techniques for automatically checking and diverting products according to at least two predetermined sorting criteria.

BACKGROUND

The invention relates to a part of an electrical connecting device, especially for use in medical technology, with a display device to display an effect on the part resulting from a preparatory step for a use of the part, a method to manufacture such a part, and the use of a substance in such a part.

SUMMARY

A large number of electrical connecting devices are used in medicine, including in operating rooms. They represent a contamination risk. As with other devices used in surgery, such as surgical instruments or items of clothing of the surgical team, connecting devices cannot be immediately used in another operation due to the contamination risk. Depending on the value of such instruments, they are either thrown away after surgery, or undergo a preparatory measure to kill as many germs as possible. For example, the rubber gloves of the surgical team are thrown away, whereas surgical instruments which are comparatively valuable are used after the preparatory measure. Electrical connecting devices used during surgery are frequently reused, and they therefore have to undergo preparatory measures before the next use.

A widespread preparatory measure is autoclaving (steam sterilization). A device to be decontaminated is exposed in an autoclave (steam pressure sterilizer) to extreme atmospheric influences such as high temperatures, high and low pressures, and high humidity. Even very resistant viruses such as hepatitis B/C or HIV (AIDS) can be reliably eliminated in this manner.

However, the connecting device is stressed by autoclaving. The coupling devices cannot be used forever; they can only be used as long as their proper function is guaranteed.

Once the proper functioning of the electrical connecting devices is no longer ensured, for example if the plug-in connection becomes loose, hazardous situations can occur such as a loss of contact power during an operation whose success is delicate. To prevent such hazardous situations from occurring in the first place, the connecting devices should or must be replaced with new parts after specific wear or loss of strength. To determine when a replacement is required, conventional connecting devices are equipped with a display in the form of a meter. Specifically, for example, a bimetal is used whose components expand differently as a function of the high temperatures arising while autoclaving. The different expansion advances the meter by 1 unit.

Such a meter is, however, quite structurally complex. In addition, it has been shown that the counting mechanism is susceptible to errors and can malfunction. In addition, the functionality is not observed in normal handling since usually a plurality of equivalent or similar connecting devices are autoclaved simultaneously, and the display of every connecting device is not checked before and after a cycle. In the case of a malfunction, a situation arises that is more problematic than a situation without a display. The user such as a surgical nurse believes that the connecting device is working properly because the display has malfunctioned, but there actually exists a high failure risk.

The invention is therefore based on the problem of offering a part of an electrical connecting device of the above-cited type whose display device has a simple construction and displays reliably.

To solve this problem, the display device has a visible field whose colored appearance changes at least in sections as a reaction to the effect of the preparatory measure. The display device is therefore subject to the same effects as the part of the connecting device itself and "measures" these effect(s) by changing its appearance. The changes are at least partially irreversible, i.e., they reverse at least over a period in time that is large in comparison to the normal life of the electrical connecting device. If they were completely reversible, the risk would exist that the effect shown by the visible field would deviate from the actual effect.

In addition, users used to colored appearances are offered a simple and pleasant means of identification. Briefly glancing at the visible field allows users to determine if they can still use the corresponding part of the connecting device, or if it should be removed and replaced with a new part. However, it is not necessary for them to notice every small change in response to a minor effect (such as only one preparatory measure). In a particularly advantageous embodiment, the change of the colored appearance from the first state to a second state is discernible with the naked eye when the effect exceeds a predetermined degree. The predetermined degree of the effect can be the degree at which the part needs to be replaced with a new part which the user can discern at a glance. The second state can also be an intermediate state that provides the user with intermediate information such as that the part has been exposed to one-half the maximum effect.

It is usefully provided that the colors differ between first and second state. For example, signaling colors can be green, yellow or red which provides the user with very simple symbolic information. It would also be conceivable for a color to weaken and appear in a different shade.

It can also be advantageous for different gray tones to appear in the first and second states. This provides a sufficient distinctive criterion which is particularly simple and economical to manufacture.

It is advantageous within the predetermined degree is at least partially determined by the maximum intensity and/or overall dose of the effect of one or a plurality of prior preparatory measures. Different effects that result from different preparatory measures can be suitably included to determine the overall dose. When the maximum intensity is the determining factor, the fact is taken into consideration that a consciously selected effect or unconsciously arising effect (such as from a defective autoclave) can substantially impair the plastic of the connecting device part. A situation that is not detectable by exclusively counting the preparatory measures is also thereby displayed to the user.

In a practical embodiment, the predetermined degree is at least partially determined by the number n of prior preparatory measures. This is a particularly useful degree that is as it were measured with an inner counter.

The number n is advantageously 1. For example, the user can identify with the naked eye when a preparatory measure has occurred. This is particularly useful when the part is only to be used a few times, especially when the initial state is the new state, and the connecting device part is already substantially impaired when the second state is reached. Particularly when the connecting device has already been used too frequently, the user is provided new warnings each time a preparatory measure is carried out.

The number n is usefully a predetermined maximum number $n_H$ of preparatory measures after which the proper functioning of the part is no longer ensured. This maximum number is typically indicated by the manufacturer of the electrical connecting device and is typically 50, 100, 200 or 500 depending on the type of electrical connecting device. In this case, the first state indicates the new state, and the second state indicates the state at which the part should be replaced with a new part.

The display device advantageously has a reference display to make it easier to see the difference, and the appearance of the reference display cannot be changed by the effect and is at least partially in the first and/or second state. For the user, the specific discernment of a colored appearance is more difficult than the relative comparison of two appearances. If the appearance of the reference display is for example in the state indicating that the part must be thrown away, the user can precisely determine when he has to throw away the part, i.e., when the appearance of the visible field or section of the visible field corresponds to the reference display. The user is accordingly given the option of exchanging the part before it is too late, but also before it is too early. Conversely, the user can also be provided with an exchange signal, i.e., that the colored appearance of the visible field or section of the visible field differs from that of the reference display, whereas there was originally no difference.

It is particularly advantageous for the display device to have a scale display with an appearance that is not changed by the effect. The scale display can be compared with the current colored appearance of the visible field or section of the visible field to determine the degree that the cumulative change differs from the colored appearance of the first state, and/or the amount of change that must occur before the second state. With the scale display, the above-cited "inner counter" of the display device is externally visible to the user. A numeric display can also be provided as a numeric translation of the color scale. In this manner, the user obtains additional useful information, for example when new parts of the electrical connecting device need to be reordered because the existing ones will soon need to be exchanged.

In addition or alternatively, it can be useful for the visual change in the colored appearance from the first state to the second state to be sudden, especially when an effect threshold is exceeded. If the user is not interested in intermediate states, he is provided the information that he finds relevant, i.e., "still works" or "does not work" in a manner that makes it unnecessary to frequently check the display device. The user continues to use the part as long as he sees a green appearance and exchanges the part as soon as he perceives a red appearance.

It is thereby useful when the effect threshold corresponds to a number $n_c$ of preparatory measures, whereby $n_c$ lies within the range of 80% of the maximum number $n_H$ and 100% of $n_H$, preferably between 90% of $n_H$ and 100% of $n_H$, and is even more preferably equal to $n_H$. In particular due to the different effects arising from different preparatory measures, the effect threshold can already be reached before reaching the maximum number of preparatory measures. This limits the loss of value from unnecessarily exchanging the part too early. A safety buffer is created at the same time.

The part of the electrical connecting device is usefully a plug, socket or cable. As long as these parts remain combined as a connecting device, the only important thing is that each connecting device has at least one part according to the invention with the display device. The intention is to provide the part with the display device where the visible field is easily seen and can be easily manufactured. However, it is also intended to provide a plurality of parts or all the parts of an electrical connecting device with a display element which can be particularly advantageous when a plurality of equivalent connecting devices get mixed up during use.

The preparatory measure(s) usefully included cleaning, sterilization and/or autoclaving. In general, the prior preparatory measure will depend on the use specified by corresponding safety guidelines. These preparatory measures can produce different effects. The effect of autoclaving is the most reliable for decontamination and is therefore preferably taken into account.

It is particularly advantageous for the display device to have a substance that responds by changing color to temperature changes, especially heat, pressure changes, especially increased pressure, and/or moisture. The color can change due to one of the cited effects, or also for example only from a combination of two or more effects.

In particular, the substance can have a coloring agent or dye, or a combination of a plurality of coloring agents or dyes. The coloring agents can be inorganic or organic and both natural and synthetic coloring agents. Either intrinsically or by the manner in which they are incorporated in the display device, these coloring agents and/or dyes are not resistant to the preparatory measure, but rather change as a result of the effect, e.g. bleed.

The invention also relates to a method to manufacture a part of an electrical connecting device, especially for medical technology, and especially a part described above. The part is made at least partially of plastic, and a substance is added to the plastic whose colored appearance changes as a reaction to an effect that results from a preparatory measure for the use of the part.

In particular, the substance is mixed with a plastic in a step in which the part is not yet completely formed. The substance can, however, also be applied to the plastic in a later step in which the part is already formed. In particular, it is intended to apply the substance as a part of a display device to the plastic in a step that follows the last manufacturing step of the part without the display device.

Another aspect of the invention relates to the use of a substance whose colored appearance changes from being exposed to an effect that results from a preparatory measure for using a part of an electrical connecting device in such a part, especially in medical technology.

Additional advantages and features of the invention are found in the following description of individual embodiments of the invention. Reference is made to FIG. 1 to 5.

BRIEF DESCRIPTION OF THE DRAWINGS

Other advantages and details of the sorting method according to at least one embodiment of the invention and devices suitable for it are found in the following explanation with reference to the drawings:

FIG. 1a is a socket, FIG. 1b a plug, FIG. 1c a cable, and FIG. 1d is a connected electrical connecting device composed of the parts in accordance with various embodiments;

DETAILED DESCRIPTION

In the following detailed description, reference is made to the accompanying drawings which form a part hereof wherein like numerals designate like parts throughout, and in which are shown, by way of illustration, specific embodiments in which the invention may be practiced. It is to be understood that other embodiments may be utilized and structural or logical changes may be made without departing from the scope of the present invention. Therefore, the following detailed description is not to be taken in a limiting sense, and the scope of the present invention is defined by the appended claims and their equivalents.

Various operations may be described as multiple discrete operations in turn, in a manner that may be helpful in understanding embodiments of the present invention; however, the order of description should not be construed to imply that these operations are order dependent.

For the purposes of the described embodiments of the instant description, the phrase "A/B" means "A or B." For purposes of the described embodiments of the instant description, the phrase "A and/or B" means "(A), (B), or (A and B)." For the purposes of the instant description, the phrase "at least one of A, B and C" means "(A), (B), (C), (A and B), (A and C), (B and C) or (A, B and C)." For the purposes of the instant description, the phrase "(A)B" means "(B) or (AB)," that is, A is an optional element.

Reference in the specification to "one embodiment" or "an embodiment" means that a particular feature, structure, or characteristic described in connection with the embodiment is included in at least one embodiment. The appearances of the phrase "in one embodiment" in various places in the specification do not necessarily all refer to the same embodiment, but it may. Furthermore, the terms "comprising," "including," "having," and the like, as used with respect to embodiments of the present invention, are synonymous.

Figure 1:
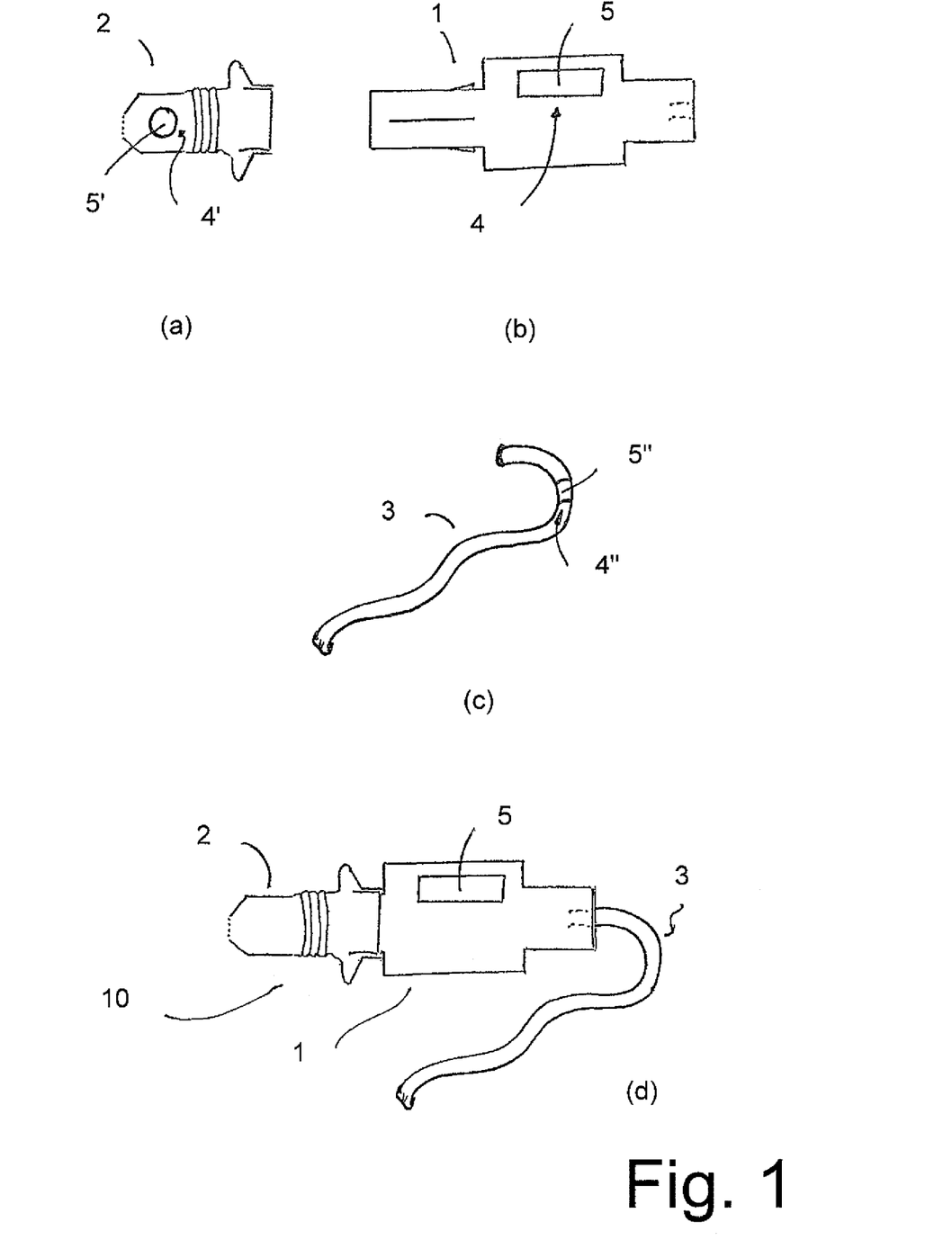
FIG. 1 illustrates a block diagram according to the invention of an electrical connecting device, i.e.

FIG. 1a shows a socket 2 of an electrical connecting device 10. The connecting device is shown connected in FIG. 1d, and it is for example designed as a push-pull plug-in mechanism. The socket 2 has a display device 4' that has an easily recognizable visible field 5'. The user of the socket 2 can use the colored appearance of the visible field 5' to see if the socket 2 is still suitable for use for example in an operating room after the prior preparatory measures, or if it needs to be replaced with a new part.

FIG. 1b shows a plug 1 that fits the socket 2 shown in FIG. 1a and forms with the socket 2 the connecting parts of the connecting device 10 shown in FIG. 1d. The plug 1 has a display device 4 that has an easily recognizable visible field 5 that serves the same purpose as the visible field 5' corresponding to the above explanations, but that has a different design (see also FIGS. 2 and 3). FIG. 1c shows a cable 3 of an electrical connecting device that has a display device 4" whose visible field 5" is designed as a strip of that surrounds the cable 3.

In FIG. 1d, we can see how a plug 1 connects with a socket 2. The socket 2 and plug 1 have cable connections, but only the cable of the plug 1 is shown with cable 3. With the connecting device 10 shown in FIG. 1d, only the plug has a display device with the visible field 5. It is also conceivable to additionally or alternatively equip the socket with the display device as shown in FIG. 1a or the cable as shown in FIG. 1c, or provide a display device with a visible field on each of the parts.

Figure 2:
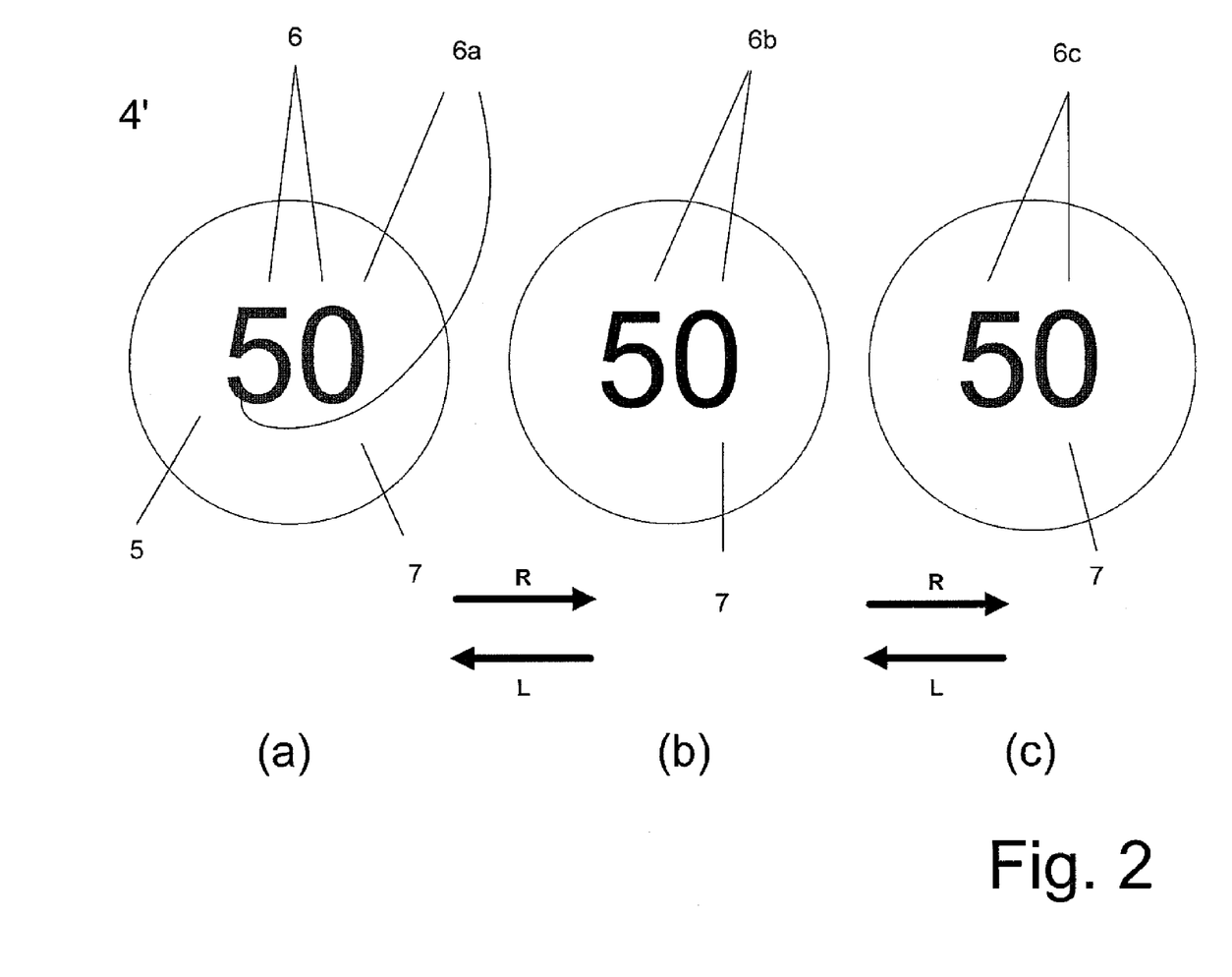
FIG. 2 illustrates a block diagram of a display device with a visible field, whereby subfigures 2a, 2b and 2c show different colored appearances of the visible field in accordance with various embodiments.

In FIG. 2, the display device 4' is an enlargement from FIG. 1a, and the appearance of its visible field 5' is in three different states. For the variant shown by time arrow R, the state shown in FIG. 2a represents the colored appearance of a new state that can be seen on a new part of an electrical connecting device. In visible field 5', two different sections can be seen, i.e. a sensitive section 6 in the form of a "50," and a reference display 7 surrounding this sensitive section 6.

In this example, the reference display 7 appears in a yellow color that is autoclavable, i.e. does not change under the effect of autoclave cycles. The sensitive section 6 contrastingly appears as a green color 6a that changes under the effect e.g. of autoclave cycles. In this case, the portrayed green 50 shows that the corresponding part of the connecting device must be replaced with a new part after 50 autoclave cycles.

FIG. 2c shows the visible field 5' after the corresponding display device 4' (together with the associated part of the connecting device) has been exposed to 50 autoclave cycles. The appearance of the sensitive section 6 has changed under the effect of the autoclave cycles such that it is also a yellow color that is equivalent to the yellow color of the reference display 7. This is indicated by the dashed lines in FIG. 2c that indicates the division of the sensitive area 6 from the reference display 7. In FIG. 2c, the actual appearance of the visible field 5' is a solid yellow. For the user, any trace of the original green 50 has disappeared. This is the signal for the user that the corresponding part of the connecting device or the entire connecting device needs to be replaced.

In this example, the change of the colored appearance of the sensitive section 6 of the visible field changes more or less evenly from the green state 6a to the yellow state 6c so that the user can also distinguish easily between a plurality of intermediate states. An example of such an intermediate state is shown in FIG. 2b where the appearance of the sensitive section 6 is a yellowish green mixed hue or a bright green 6b.

It is clear that instead of the different colors of yellow and green, other colors can be used as long as it is ensured that the appearance of the final state 6c corresponds with the reference display 7. It is also conceivable for the number 50 to be initially identifiable as a dark gray tone in comparison to a light gray tone of the reference display 7, and after 50 autoclaving cycles, has the same gray tone as the reference display. In particular, the reference display 7 can be formed by the plastic outer sleeve of the part of the connecting device.

In another embodiment of the invention, the colored appearance of the display device 4' changes according to the time bars I. First, the entire visible field 5' has a uniform appearance. Only after a few autoclaving cycles is the change in the sensitive section 6 discernible whose appearance for example changes over an intermediate step 6b to an appearance 6a that is clearly different from the appearance of the reference display 7. In this case, the warning is increased by the fact that the resulting appearance 6a of the sensitive section 6 is red (after 50 preparation cycles).

According to the above-presented principle, there are only a few limits to the color and shape so that, for example, a different symbol beside the number 50 or another number can be used that for example indicates a maximum number of preparation measures.

Figure 3:
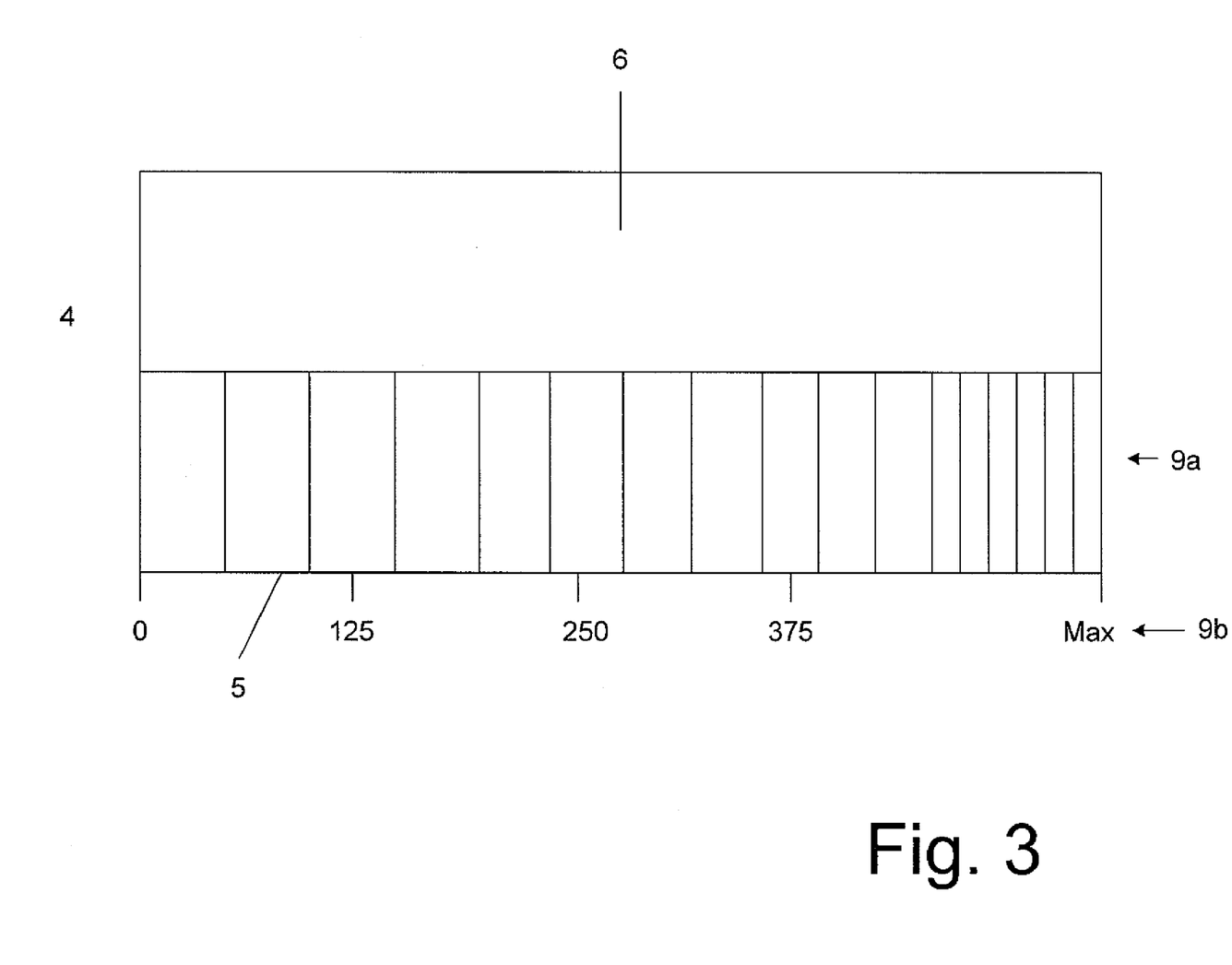
FIG. 3 illustrates a block diagram of a display device of a part according to the convention in accordance with various embodiments.

FIG. 3 shows another embodiment of a display device 4 with a visible field 5. In this case, a sensitive section 6 and a scale display 9 can be seen in the visible field 5. As already noted in the above description, the initial appearance of the sensitive section 6 changes after autoclaving cycles so that it appears as a color that is different from the original color that can be distinguished by the naked eye, in this case for example after $n_H$=500 autoclaving cycles. Of course, intermediate states can also be distinguished with the naked eye as is especially the case with this embodiment.

The scale display 9 has a color scale 9a that is associated with a numeric scale 9b such that it assigns the numbers to colored appearances that corresponded to the colored appearance of sensitive section 6 after a corresponding number of autoclaving cycles. The color scale 9a is composed of these colors.

The user can therefore easily determine the number of prior autoclaving cycles from the visible field 5 of the display device 4 shown in FIG. 3 by comparing the current appearance of the sensitive section 6 with the corresponding scale range of the color scale 9a by using the numeric scale 9b. The user then knows how many times he can still use the corresponding part of the electric connecting device or the entire connecting device before reaching the limit indicated by the manufacturer ($n_H$=500 in this case). The user can thereby obtain a reliable indication of the remaining potential use of his electrical connecting device and order a replacement at the right time before the maximum number of 500 is exceeded.

Figure 4:
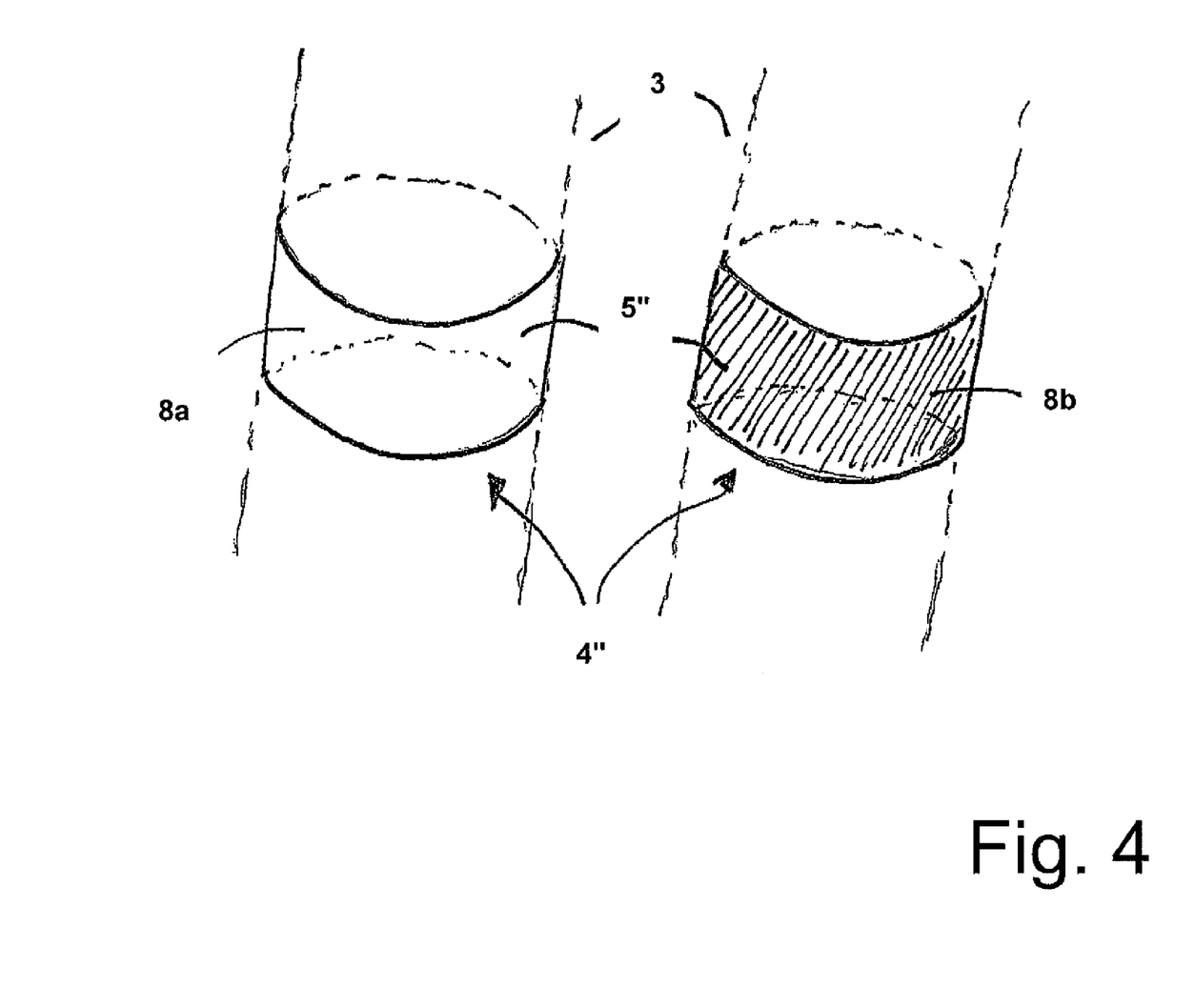
FIG. 4 illustrates a block diagram display device of a part according to the invention in accordance with various embodiments.

FIG. 4 shows another embodiment of a display device 4" whose visible field 5" surrounds the part of the connecting device that in this example is the cable 3 in FIG. 1c. The mode of operation of this display device is somewhat different than that of the above-described display devices in that the colored appearance 8a of the visible field 5 changes only minimally with each autoclaving cycle so that the naked eye scarcely discerns a difference from the original appearance 8a. The visible change of the colored appearance 8a to the colored appearance 8b shown in FIG. 4b occurs suddenly after an effect threshold is exceeded that, in this example, precisely corresponds to the maximum number of autoclaving cycles (100) for which the corresponding part of the connecting device or the entire connecting device is designed.

In this example, the colored appearance 8b is very dark, whereas colored appearance 8a is very light and for example corresponds to the colored appearance of the cable 3. The display device 4" is disposed on the cable 3 such that the user immediately sees when the appearance of the surrounding strip-shaped visible field 5" has become dark each time the cable is run and the connecting devices connected. The user then knows that he needs to replace the cable 3 or the entire electrical coupling device.

In addition, the visible field 5" can be designed so that the transition to the colored appearance 8b occurs a few autoclaving cycles before the actual limit of autoclaving cycles indicated by the manufacturer (100), e.g., after 80 or 90 autoclaving cycles. In this manner, an intrinsic safety buffer is incorporated corresponding to the difference of autoclaving cycles, i.e., in this example 20 or 10 autoclaving cycles. If the connecting device is used a few more times after the dark appearance 8b of the visible field 5", the user is still in the safe range, i.e., the coupling device is still guaranteed to work properly even though the appearance of the visible field 5" has already changed. A plurality of changes of the color and shape are also possible. For example, a red text can appear after a specific effect threshold that notifies the user that he may no longer use the part.

Figure 5:
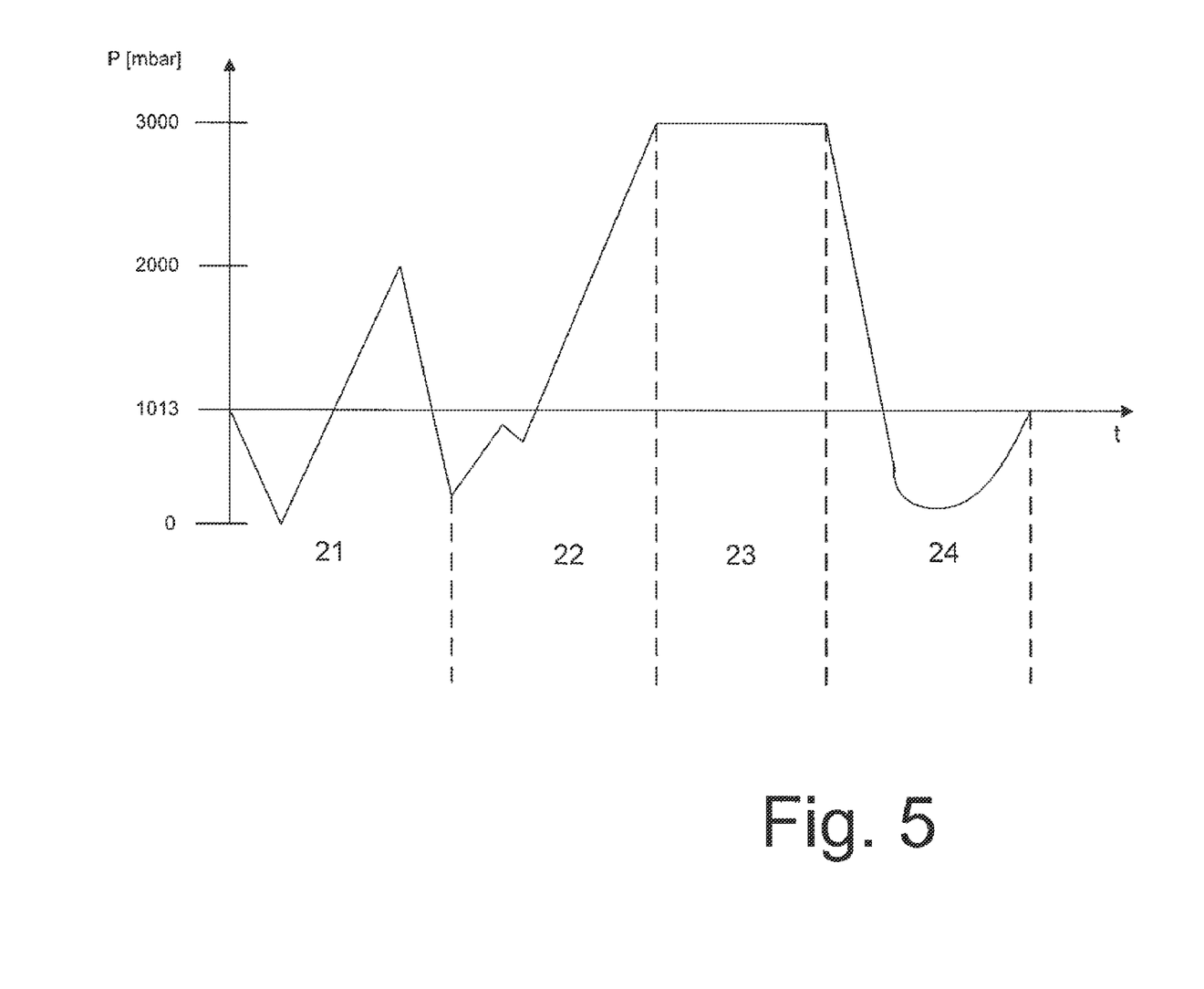
FIG. 5 illustrates a block diagram of a preparatory measure for a part according to the invention in accordance with various embodiments.

Finally, FIG. 5 shows the pressure curve overtime that occurs with a typical autoclaving cycle in an autoclave. In a first venting phase 21, an initial preliminary vacuum phase is followed by a rise in pressure and then drop in pressure to a second preliminary vacuum phase. In a pressure buildup phase 22, the pressure is increased to a maximum of approximately 3 bar, and the temperature is raised in this phase to approximately 134° C. In the actual sterilization phase 23 this temperature is held for approximately 5 minutes followed by 15 minutes of 121° C., and a pressure of approximately 3 bar is held during the entire sterilization phase 23. Finally, the pressure is decreased in the drying phase 24 including a subsequent vacuum phase for drying followed by ventilation. The substance used for the sensitive section in the display device preferably reacts to the temperature and/or pressure during the sterilization phase 23 in the autoclave.

The embodiments in the figures only represent a few possible examples of realizing a part according to the invention of an electric connecting device. Accordingly, the features of the invention disclosed in the above description and claims can be essential both by themselves and in any combination for the realization of the invention in its various embodiments.

What is claimed is:

1. An electrical connecting device comprising:
   a display device to display an effect on the device resulting from a preparatory operation to use the device, the display to include a visible field whose colored appearance changes at least in sections as a reaction to the effect resulting from the preparatory operation;
   wherein the colored appearance changes include the colored appearance changing from a first state to a second state, wherein a difference in the first and second states is discernible by a human viewer when the effect exceeds a predetermined degree;
   wherein the predetermined degree is at least partially determined by a number of prior preparatory operations; and
   wherein the number of prior preparatory operations is a predetermined maximum number of prior preparatory operations after which the proper functioning of the device is no longer ensured.

2. The electrical connecting device of claim 1 wherein different colors appear in the first and second states.

3. The electrical connecting device of claim 1 wherein different gray levels appear in the first and the second states.

4. The electrical connecting device of claim 1 wherein the predetermined degree is at least partially determined by a maximum intensity and/or an overall dose of the effect of one or a plurality of prior preparatory operations.

5. The electrical connecting device of claim 1 wherein the maximum number is selected from the group consisting of 1, 50, 100, 200 or 500.

6. The electrical connecting device of claim 1 wherein the visible change from the colored appearance of the first state to the second state occurs suddenly, and the number of prior preparatory operations is equal to a threshold number of prior preparatory operations, the threshold number selected from a range of numbers between 80% of a predetermined maximum number of preparatory operations and 100% of the predetermined maximum number.

7. The electrical connecting device of claim 6 wherein the threshold number is selected from a range of numbers between 90% and 100% of the maximum number.

8. The electrical connecting device of claim 1 wherein the display device has a reference display, and the appearance of the reference display does not change under the effect and is at least partially in the first and/or second state.

9. The electrical connecting device of claim 1 wherein the display device has a scale display with an appearance that does not change under the effect, and the scale display can be compared by the human viewer with a current colored appearance of the visible field or section of the visible field to determine a degree an existing change differs from the colored appearance of the first state, and/or an amount of change that occurs before reaching the second state.

10. The electrical connecting device of claim 1 wherein the visible change from the colored appearance of the first state to the second state occurs suddenly, when an effect threshold is exceeded.

11. The electrical connecting device of claim 1 wherein the electrical connector is selected from a group consisting of a plug, a socket, or a cable.

12. The electrical connecting device of claim 1 wherein the preparatory operation is a selected one from the group consisting of cleaning, sterilization and autoclaving.

13. The electrical connecting device of claim 1 wherein the display device includes a substance that changes color in response to a selected one of temperature change, heat, pressure change, increased pressure, and moisture.

14. The electrical connecting device of claim 1 wherein the device is made at least partially of plastic and a substance is added to the plastic whose colored appearance changes as a reaction to an effect that results from the preparatory operation.

* * * * *